(12) United States Patent
Banks et al.

(10) Patent No.: US 10,932,487 B2
(45) Date of Patent: Mar. 2, 2021

(54) VAPORISABLE MATERIAL

(71) Applicant: JT International S.A., Geneva (CH)

(72) Inventors: Geoff Banks, Ballymena (GB); Kelly Crawford, Ballymena (GB); Ugurhan Yilmaz, Southampton (GB)

(73) Assignee: JT International S.A.

( * ) Notice: Subject to any disclaimer, the term of this patent is extended or adjusted under 35 U.S.C. 154(b) by 0 days.

(21) Appl. No.: 16/678,176

(22) Filed: Nov. 8, 2019

(65) Prior Publication Data

US 2020/0068945 A1 Mar. 5, 2020

Related U.S. Application Data

(62) Division of application No. 14/888,311, filed as application No. PCT/EP2014/058989 on May 2, 2014, now abandoned.

(30) Foreign Application Priority Data

May 2, 2013 (EP) ..................................... 13166239

(51) Int. Cl.
*A24F 47/00* (2020.01)
*A24B 13/00* (2006.01)
(Continued)

(52) U.S. Cl.
CPC .............. *A24B 13/00* (2013.01); *A24B 15/10* (2013.01); *A24B 15/16* (2013.01); *A24B 15/167* (2016.11); *A24D 1/14* (2013.01); *A24F 23/00* (2013.01); *A24F 47/004* (2013.01); *A61M 11/041* (2013.01); *A61M 11/042* (2014.02); *A61M 11/047* (2014.02); *A61M 11/048* (2014.02); *A61M 15/0021* (2014.02); *A61M 15/0028* (2013.01); *A61M 15/0035* (2014.02); *A61M 15/0041* (2014.02); *A61M 15/06* (2013.01);
(Continued)

(58) Field of Classification Search
CPC .................................. A24B 15/16; A24D 1/14
See application file for complete search history.

(56) References Cited

U.S. PATENT DOCUMENTS

| 4,938,236 A | 7/1990 | Banerjee et al. |
| 5,067,499 A | 11/1991 | Banerjee et al. |

(Continued)

FOREIGN PATENT DOCUMENTS

| CA | 2807331 A1 | 2/2012 |
| DE | 10-2009-060449 A1 | 6/2011 |

(Continued)

OTHER PUBLICATIONS

British Examination Report for Application No. GB1307942.1 dated Aug. 2, 2017, 4 pages.

(Continued)

*Primary Examiner* — Eric Yaary
(74) *Attorney, Agent, or Firm* — Lerner, David, Littenberg, Krumholz & Mentlik, LLP

(57) ABSTRACT

A vaporisable material for use in a vapour-generating device comprising tobacco having a moisture content of from about 3 to 5 wt %, and further comprising a humectant in an amount of at least 20 wt % is disclosed. The invention also relates to use of the vaporisable material in a vapour-generating device, and to a sealed package containing the vaporisable material and a device containing the sealed package of vaporisable material.

7 Claims, 2 Drawing Sheets

(51) Int. Cl.
    *A61M 15/00* (2006.01)
    *A24D 1/14* (2006.01)
    *A24B 15/167* (2020.01)
    *A61M 15/06* (2006.01)
    *A61M 11/04* (2006.01)
    *A24B 15/16* (2020.01)
    *A24B 15/10* (2006.01)
    *A24F 23/00* (2006.01)

(52) U.S. Cl.
    CPC ............ *A61M 2205/0266* (2013.01); *A61M 2205/125* (2013.01); *A61M 2205/3653* (2013.01); *A61M 2205/584* (2013.01); *A61M 2205/8206* (2013.01)

(56) References Cited

U.S. PATENT DOCUMENTS

| | | |
|---|---|---|
| 2005/0066985 A1 | 3/2005 | Borschke et al. |
| 2007/0012328 A1 | 1/2007 | Winterson et al. |
| 2007/0023056 A1 | 2/2007 | Cantrell et al. |
| 2007/0074734 A1 | 4/2007 | Braunshteyn et al. |
| 2007/0102013 A1 | 5/2007 | Adams et al. |
| 2008/0029110 A1 | 2/2008 | Dube et al. |
| 2009/0025738 A1 | 1/2009 | Mua et al. |
| 2009/0293892 A1 | 12/2009 | Williams et al. |
| 2014/0076337 A1 | 3/2014 | Woodman et al. |
| 2014/0166032 A1 | 6/2014 | Gindrat |
| 2015/0181938 A1 | 7/2015 | Metrangolo et al. |

FOREIGN PATENT DOCUMENTS

| | | |
|---|---|---|
| EP | 0520231 A2 | 12/1992 |
| EP | 2338360 A1 | 6/2011 |
| WO | 2009079641 A2 | 6/2009 |
| WO | 2012132008 A1 | 10/2012 |

OTHER PUBLICATIONS

British Search Report for Application No. GB1307942.1 dated Oct. 31, 2013, 1 page.

International Search Report for Application No. PCT/EP2014/058989 dated Jul. 7, 2014.

The Karl Fischer titration method is described in Fischer, K., Angew. Chem. (1935) 48 (26): 394-396 (English Abstract provided).

VAPORISABLE MATERIAL

CROSS-REFERENCE TO RELATED APPLICATIONS

The present application is a divisional application of U.S. patent application Ser. No. 14/888,311, filed on Oct. 30, 2015, which is a national phase entry under 35 U.S.C. § 371 of International Application No. PCT/EP2014/058989, filed May 2, 2014, which claims priority from EP Patent Application No. 13166239.7 filed May 2, 2013, all of which are incorporated herein by reference.

BACKGROUND OF THE INVENTION

The present invention relates to vaporisable material for use in a vapour-generating device. Devices which heat rather than burn vaporisable material, such as those containing tobacco, to create a vapour for inhalation are becoming popular. They generally comprise a heat source powered by gas or electricity and a chamber for receiving vaporisable material containing a vapour-generating product. In use the material is inserted into the device and heated by the heat source to generate a vapour for inhalation. An example of such a device can be found in PCT publication WO 2009/079641.

Such devices and the material for use in them have become popular because they can provide a user with an experience very similar to smoking the vaporisable material without the burning of plant material such as tobacco.

However, such devices are not always popular with consumers because they produce inconsistent levels of vapour and are often unreliable in terms of the length of use of the vaporisable material, as well as providing inconsistent and unreliable flavour/taste delivery to a user.

The present invention seeks to provide vaporisable material for use in the vapour-generating device, that material providing a far higher degree of consistency and quality of flavour to an end user.

BRIEF SUMMARY OF THE INVENTION

According to a first aspect, the present invention provides a vaporisable material for use in a vapour-generating device, comprising tobacco having a moisture content of from about 3 to 5 wt %, and further comprising a humectant in an amount of at least 20 wt %.

According to a second aspect, the present invention provides a sealed package containing vaporisable material according to the first aspect of the invention.

According to a third aspect, the present invention is directed to the use of vaporisable material as defined in the first aspect of the invention in a vapour-generating device.

According to a fourth aspect, the present invention provides a vapour-generating device comprising vaporisable material as defined according to the first aspect of the invention.

DETAILED DESCRIPTION

Figure 1:
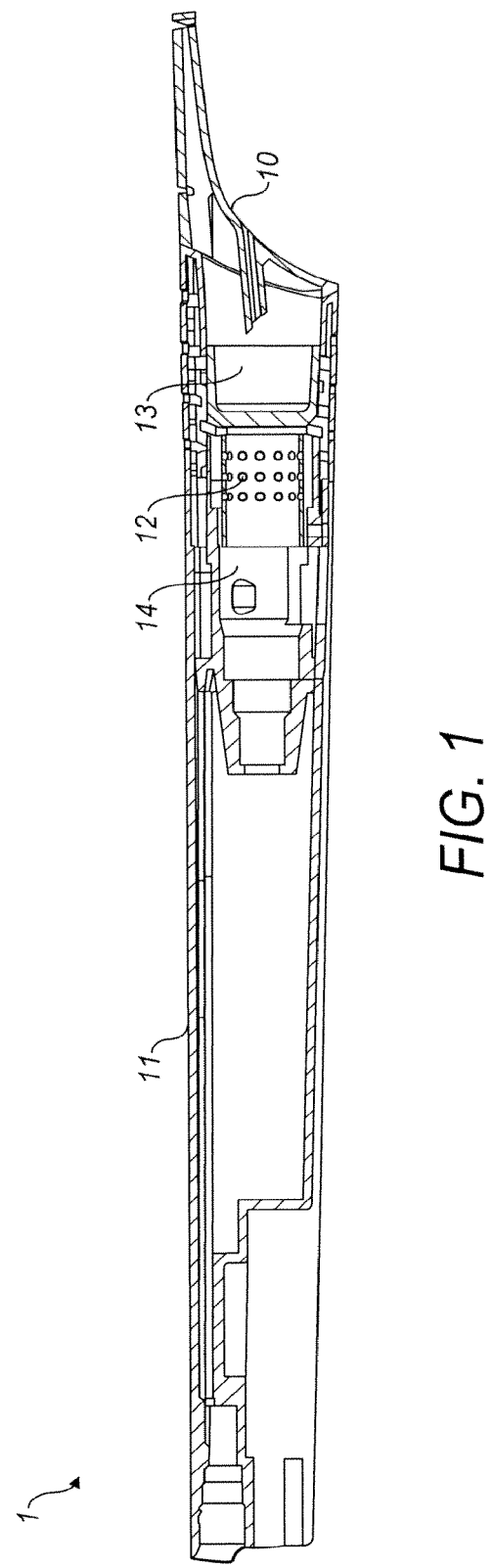
FIG. 1 is a side cross-sectional schematic view of a heating device comprising a capsule according to the present invention.

As used herein, the term "moisture content" refers to the amount of moisture (i.e. water) present in a given material, e.g. vaporisable material, including plant material such as tobacco.

As used herein, the term "vaporisable" has its usual meaning in the art, referring to a material that is capable of being converted to from a solid or liquid state to a gaseous state upon heating.

Moisture content is an important parameter of the chemical composition of vaporisable materials, and in particular of the plant material such as tobacco. The moisture content of vaporisable materials, and the components of vaporisable materials, may affect various properties of the material, including:

Ease of particle size reduction, with drier materials being easier to mill into fine powders;

Texture and density, with wetter materials being of higher density and more sticky; and Efficiency of vapour production upon heating, since the moisture content affects the time and energy required for the vaporisable material and/or components thereof to reach the desired vaporisation temperature.

In addition, the present inventors have observed that the mouthpiece portion of a vapour-generating device becomes hot if the moisture content of the tobacco component of the vaporisable material is elevated. This is believed to be due to the tendency of water contained in the vapour to transfer heat from the oven or heat source to the mouthpiece.

The inventors have also observed that reducing the moisture content of the tobacco component of the vaporisable material can affect the flavour and/or taste of the vaporisable material when it is inhaled by a user. The flavour and/or taste of tobacco can become harsh and unpleasant if the moisture content is too low.

Therefore, the present invention provides a vaporisable material suitable for use in a vapour-generating device, comprising tobacco having a moisture content of from about 3 to 5 wt %. Preferably, the tobacco has a moisture content of about 4 wt %. For the avoidance of doubt, these wt % values are based on the total weight of the tobacco component only; these wt % values are not based on the total weight of the vaporisable material.

Examples of suitable forms of tobacco include leaf, STEM, expanded tobacco blend and reconstituted tobacco blend.

The inventors have also observed that the vaporisable material of the invention when used in a vapour-generating device can significantly reduce or avoid noise generation when heated to produce a vapour.

It is proposed by the present inventors that since flavour ratio is defined based on tobacco weight, lower moisture content results in more perceived flavour levels on the first puff on a vapour-generating device containing the vaporisable material, compared to tobacco material having higher moisture levels, due to less dilution of the vapour in the low moisture-containing material. Furthermore, higher moisture results in less vapour volume in the first puffs, which creates a poor first puff impression and is unsatisfactory for consumers. In addition, the inventors have found that vaporisable material comprising tobacco that has a moisture content lower than about 3 wt % has a harsh taste and is associated with increased irritation when inhaled. These observations are surprising, since it is unexpected that the optimum moisture content of the tobacco component of a vaporisable material should be found to be lower than the optimum moisture content of a material that is burnt in use (such as a cigarette, which has an optimum moisture content of about 12.5 wt %).

As used herein, the term "taste" has its usual meaning, and refers to the chemical sensation produced when inhaled vapours produced by heating the vaporisable material of the invention reacts chemically with taste bud receptors in the mouth of a user. The sensation of taste can be categorized into five basic tastes: sweetness; sourness; saltiness; bitterness; and umami. Taste, along with smell (olfaction) and trigeminal nerve stimulation, determines perception of flavours. The term "flavour", as used in the context of the present invention, refers to the sensory impression of inhaled vapours perceived by a user, and is determined mainly by the chemical senses of taste and smell.

The skilled person will be familiar with suitable methodologies for determining the moisture content of a plant material, such as tobacco, and will appreciate that different methodologies are applicable to different materials. For the avoidance of doubt, a method for determining the moisture content of tobacco is described as follows:

A heat source, preferably a halogen lamp, is set to a temperature of 105° C. and ~2 g of tobacco sample is placed in a weighing chamber and heated by the lamp. The weight of the sample due moisture loss is measured until a constant weight is reached. The moisture content is calculated by subtracting the dried sample weight ($W_D$) from the initial sample weight ($W_I$), dividing by the dried sample weight, and multiplying by 100:

$$\frac{W_D - W_I}{W_D} \times 100$$

A vaporisable material according to the invention comprises tobacco having a moisture content as described herein and also comprises a humectant.

A humectant is a hygroscopic substance that has an affinity to form hydrogen bonds with molecules of water and is used to produce a visible exhaled aerosol (i.e. vapour) when the product is in use. Suitable humectants for inclusion in a vaporisable material according to the present invention include propylene glycol, also known as 1,2-propanediol or propane-1,2-diol and having the formula $C_3H_8O_2$ or $HO-CH_2-CHOH-CH_3$, and glycerol, also known as glycerine and having the formula $C_3H_8O_3$. In a preferred embodiment, the humectant is propylene glycol.

The vaporisable material of the invention comprises at least 20 wt % of a humectant, and preferably the amount of humectant present is from 20 to 60 wt %, most preferably about 40 to 50 wt %. These wt % values are based on the total weight of the vaporisable material, including the tobacco material and the humectant.

With the addition of humectants, the moisture content of the vaporisable material differs from blend to blend, but it is preferably within the range of 1 to 4 wt %, when the moisture content of the tobacco component lies in the range from about 3 to 5 wt % and the amount of humectant ranges from about 20 wt % to about 60 wt %. In general, the overall wt % moisture content of the vaporisable material comprising tobacco material and humectant will be lower than the moisture content of the tobacco material alone, due to humectants having low moisture content.

As the skilled person in the art will be aware, the moisture content of a final vaporisable tobacco product may be obtained by Karl Fischer titration, following extraction of the vaporisable material in a suitable solvent such as methanol, or by heating the vaporisable material in a Stromboli sample oven. The Karl Fischer titration method is described in Fischer, K., *Angew. Chem.* (1935) 48 (26): 394-396.

The vaporisable material of the invention is suitable for use in a vapour-generating device, such as a tobacco-heating device. An example of such a device can be found in PCT publication WO 2009/079641.

In a preferred embodiment, the device is capable of maintaining the moisture content of the tobacco component of the vaporisable material within the range of from about 3 to 5 wt %, and most preferably about 4 wt %.

The present inventors have observed that when a vaporisable material as defined herein is inhaled using a vapour-generating device, higher moisture contents of the material correspond to an increased harshness in the flavour. This is thought to be due to condensed water droplets in the aerosol evaporating much faster than either propylene or glycol (i.e. the humectant component of the product). Nicotine present in the water droplets also evaporates, and the gaseous nicotine causes increased harshness in the taste/flavour of the inhaled product.

The vaporisable material is preferably provided in a sealed package, which functions as an absolute barrier enabling the moisture content and flavour to be retained over time. The term "sealed package" refers to a gas-impermeable container having a hermetic closure and in the context of the present invention is preferably a capsule. The sealed package is configured to be made open ready to release a vapour when heated by a vaporising device. Ideally, the vaporisable material should be processed and packaged as quickly as possible to ensure that atmospheric moisture is not absorbed into the material.

Referring to FIG. 1, there is shown a tobacco heating device 1 of the type generally described in PCT publication WO 2009/079641. The device has a mouthpiece 10, body 11, heater 12, heating chamber 13 and a fuel supply 14. The device also usually has control components to regulate the temperature of the device particularly within the heating chamber to control a container 20 placed within the device in use. Whilst this example device uses a combustible fuel as a heat source, it will be appreciated that the device may have another type of heat source and power supply, such as an electrical heater and battery, for example.

In use a capsule 20 is inserted into the heating chamber 13, and the heater 12 supplied with fuel from the fuel tank 14 to heat the heating chamber 13, under the control of a user. The capsule 20 contains a plug of vaporisable material comprising tobacco material having a moisture content of from about 3 to 5 wt %, in accordance with the present invention. The contents of the capsule are heated by the heater 12 to create an aerosol vapour based on the contents of the container, that aerosol then being inhaled by the user via the mouth piece 10.

Figure 2:
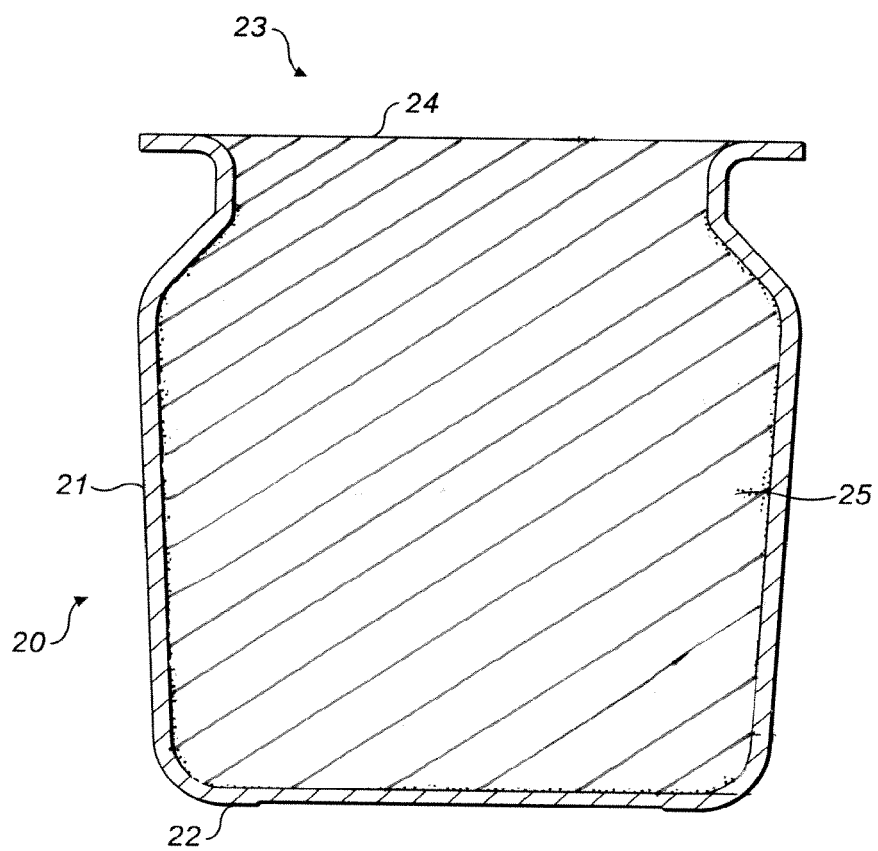
FIG. 2 is a side cross-sectional view through a plug and capsule in accordance with the invention.

Referring to FIG. 2, a plug of vaporisable material 25 comprising tobacco material having a moisture content of from about 3 to 5 wt % according to the invention is shown. In this example the plug is provided in a capsule 20. It is possible to provide the plug in a user-removable wrapper which is taken off prior to insertion of the plug 25 into the heating chamber 13 of the device 1 or to supply the plug 25 in a dispenser which inserts the plug 25 into the device 1 to avoid handling by a user.

The invention claimed is:
1. A vapour-generating system comprising:
 a gas-impermeable container comprising a plug of a vaporisable material, wherein the vaporisable material comprises tobacco having a moisture content of about 1 to 5 wt %, and a humectant content of about 20 to 60 wt %, and a chamber arranged to receive the gas-impermeable container and generate a vapour by heating the chamber.

2. The vapour-generating system according to claim 1, wherein the gas-impermeable container is a capsule.

3. The vapour-generating system according to claim 1, wherein the gas-impermeable container is configured to be made open ready to release the vapour when heating without burning of the vaporisable material.

4. The vapour-generating system according to claim 1, wherein the humectant is propylene glycol or glycerol.

5. The vapour-generating system according to claim 1, wherein the tobacco has a moisture content of about 3 to 5 wt %.

6. The vapour-generating system according to claim 1, wherein the humectant content is about 40 to 50 wt %.

7. The vapour-generating system according to claim 1, further comprising a temperature control component to regulate temperature of the chamber.

\* \* \* \* \*